United States Patent [19]
Delonzor et al.

[11] Patent Number: 5,830,136
[45] Date of Patent: Nov. 3, 1998

[54] GEL PAD OPTICAL SENSOR

[75] Inventors: Russell L. Delonzor, Union City; Jason Gentry, Castro Valley; Michael E. Fein, Mountain View; Albert L. Ollerdessen, San Rafael; Richard K. Spero, Brentwood, all of Calif.

[73] Assignee: Nellcor Puritan Bennett Incorporated, Pleasanton, Calif.

[21] Appl. No.: 741,956

[22] Filed: Oct. 31, 1996

[51] Int. Cl.$^6$ ............................................. A61B 5/00
[52] U.S. Cl. .......................................... 600/323; 600/344
[58] Field of Search .................................. 600/310, 322, 600/323, 344, 473, 476, 338; 524/476

[56] References Cited

U.S. PATENT DOCUMENTS

| | | | |
|---|---|---|---|
| 4,369,284 | 1/1983 | Chen | 524/476 |
| 4,391,278 | 7/1983 | Cahalan et al. | 128/640 |
| 4,593,053 | 6/1986 | Jevne et al. | 523/111 |
| 4,600,261 | 7/1986 | Debbaut | 339/116 |
| 4,618,213 | 10/1986 | Chen | 350/96.34 |
| 4,634,207 | 1/1987 | Debbaut | 339/116 |
| 4,643,924 | 2/1987 | Uken et al. | 428/35 |
| 4,685,464 | 8/1987 | Goldberger et al. | 128/633 |
| 4,890,619 | 1/1990 | Hatschek | 128/633 |
| 4,975,175 | 12/1990 | Karube et al. | 204/403 |
| 5,054,488 | 10/1991 | Muz | 128/633 |
| 5,109,849 | 5/1992 | Goodman et al. | 128/633 |
| 5,140,746 | 8/1992 | Debbaut | 29/855 |
| 5,262,468 | 11/1993 | Chen | 524/476 |
| 5,299,570 | 4/1994 | Hatschek | 128/633 |
| 5,337,744 | 8/1994 | Branigan | 128/633 |
| 5,377,673 | 1/1995 | Van Dell et al. | 128/633 |
| 5,394,877 | 3/1995 | Orr et al. | 128/662 |
| 5,402,777 | 4/1995 | Warring et al. | 604/307 |
| 5,402,778 | 4/1995 | Chance | 128/633 |
| 5,452,717 | 9/1995 | Branigan et al. | 128/633 |

OTHER PUBLICATIONS

Brochure entitled "3M Refastenable Tape Closure System", Health Care, 3M 1993, 70–2008–6676–5 (63.2).

Brochure entitled "Malleolar Protective Sleeve and Brace Liner", Silipos, Niagara Falls, New York.

*Primary Examiner*—John P. Lacyk
*Assistant Examiner*—Eric F. Winakur
*Attorney, Agent, or Firm*—Townsend and Townsend and Crew LLP

[57] ABSTRACT

An improved sensor using a gel. In one aspect, the gel is an oil plasticized thermoplastic elastomer gel. In one embodiment, the gel is mineral oil-based. The gel may be embedded on a support layer. Means for reducing shunted light from the gel are provided, such as substantially opaque material in the gel or breaks in the gel.

58 Claims, 3 Drawing Sheets

GEL PAD OPTICAL SENSOR

BACKGROUND OF THE INVENTION

The present invention relates to optical sensors using a gel for application to a patient, and in particular to pulse oximeter sensors.

Many types of optical sensors are used to measure physiological characteristics of a patient. Typically, an optical sensor provides emitted light which is then scattered through tissue and detected. Various characteristics of a patient can be determined from analyzing such light, such as oxygen saturation, pulse rate, pH, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Some pulse oximetry sensors use adhesive gels to attach the sensor to a patient. For example, U.S. Pat. No. 5,054,488 to Muz shows gel pads placed directly over the emitter and detector. The gel is described as being a silicone-based gel that is transparent and is used for an adhesive.

Another use of a gel adhesive is shown in U.S. Pat. No. 5,377,673 to Van Del. Transparent, water-based gel adhesives are described. These are used for a fetal sensor and are placed over the attaching surface of the sensor. The gels are described as colloids which are transparent and are easily washed off. U.S. Pat. No. 5,394,877 discusses a mesh reinforced hydrogel film used with an ultrasound device.

Gel sensors are desirable for patients with sensitive skin. A normal, adhesive type sensor may tear sensitive skin upon being removed. Accordingly, a gel adhesive is desirable for fetuses, infants, burn victims, etc. It is desirable also to have a gel which is easy to handle and does not produce other adverse effects. For example, hydrogels tend to dry out quickly and are hard to sterilize. Allergic reactions are another concern. For example, many people are allergic to latex-based adhesives.

SUMMARY OF THE INVENTION

The present invention provides an improved optical sensor using a gel. In one aspect, the gel is an oil plasticized thermoplastic elastomer gel. In one embodiment, the gel is mineral oil-based.

In one embodiment, a woven scrim has the gel embedded onto it for ease of handling. Preferably, holes are opened in the gel over the emitter and detector to improve optical transmission and to prevent shunting of light. Additionally, the gel may have pigment, dye or other material incorporated in it to attenuate light at the desired wavelengths to further prevent shunting through the gel layer.

In one embodiment, a gel may be imbedded with electrically conductive material to provide an EMI shield. The gel may be placed on a thin support layer, and wrapped around a patient's finger or other appendage, with an attachment mechanism, such as Velcro™, closing the sensor by attaching one end to the back of the sensor, without requiring adhesive attachment to the patient's skin. The gel preferably has sufficient thickness to spread the heat from the emitter and limit the peak temperature caused by heat imparted to the patient's skin. The gel is preferably insoluble in water to seal out water-based contaminants. The gel is preferably sufficiently compressible and conformable to distribute high pressure being applied to the patient, thus avoiding pressure irritation or trauma to the skin.

For a further understanding of the nature and advantages of the invention, reference should be made to the following description taken in conjunction with the accompanying drawings.

DETAILED DESCRIPTION OF THE PREFERRED EMBODIMENTS

Figure 1:
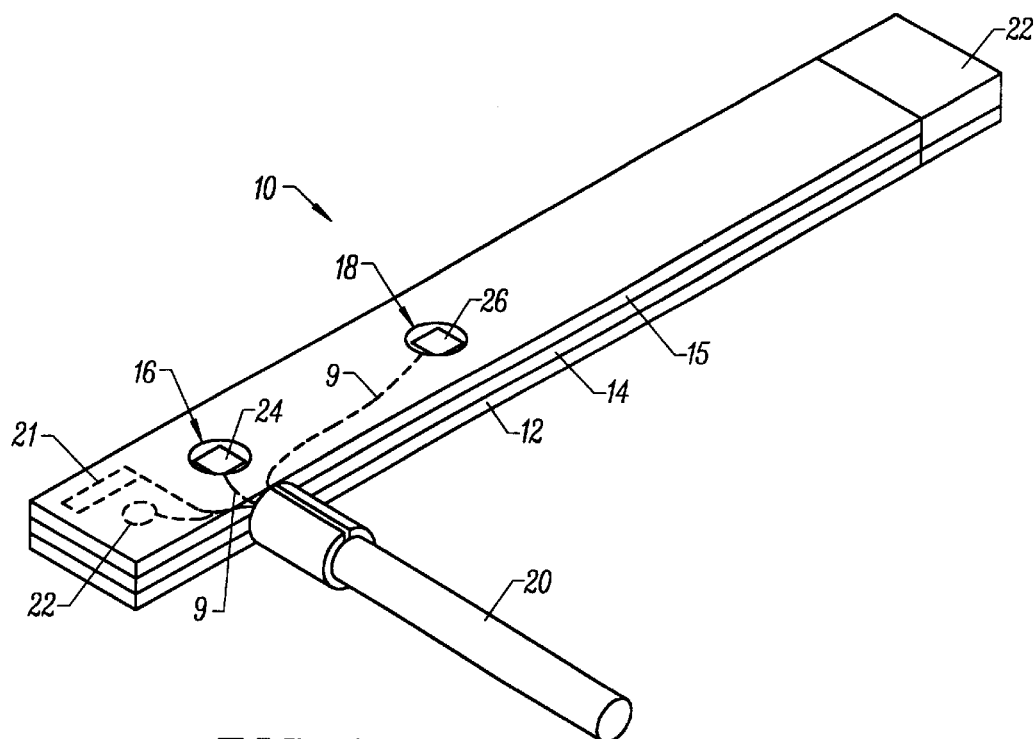
FIG. 1 is a perspective view of a gel pad sensor according to the present invention.

FIG. 1 illustrates one embodiment of a sensor 10 according to the present invention. The sensor includes a cover layer 12 (e.g., polyurethane), on top of which a gel support layer 14 is mounted, with a gel layer 15 on top of support layer 14. Openings 16 and 18 are left in the gel layer over an emitter 24 and a detector 26 mounted on cover layer 12. A cable 20 attaches to the emitter and detector via traces or wires 9 on cover layer 12. An attachment surface 22 is provided for adhering to the back side of cover layer 12 when the sensor is wrapped around a patient's finger or other appendage. In one embodiment, portion 22 may be a series of low curvature hooks for attaching to a woven or looped material on the backside of cover layer 12, such as a Velcro™ fastener. FIG. 1 also shows an optional calibration impedance or other device 21, which can indicate the wavelength of an emitter, or a set of coefficients to be used for the emitter (such as is shown in U.S. Pat. No. 4,621,643, the disclosure of which is hereby incorporated herein by reference). Also shown is an optional additional sensor 22, such as an EKG, a pressure sensor, or a $CO_2$ sensor.

Figure 2:
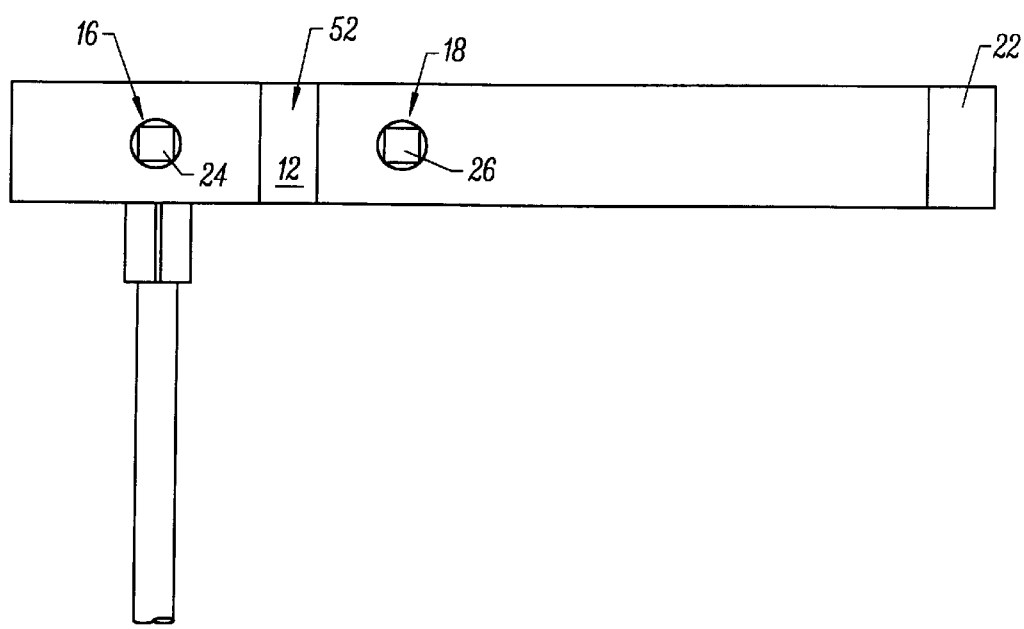
FIG. 2 is a top view of an embodiment of a sensor showing a shunt-avoiding gap in the gel layer.

FIG. 2 is a top view of an embodiment of a sensor including a gap 52 for reducing light shunting from the emitter to the detector through gel layer 15, as discussed in more detail below.

Figure 3:
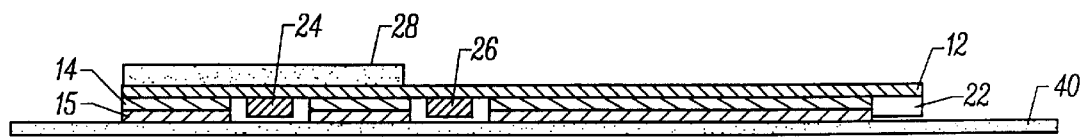
FIG. 3 is a side, cutaway view of the sensor of FIG. 1 with an added release liner and attachment layer.

FIG. 3 is a side, cutaway view of the embodiment of FIG. 1 on a protective release liner 40. FIG. 3 shows an emitter 24 and a detector 26 mounted on cover layer 12 and surrounded by gel layer 15, with gel layer 15 being mounted on gel support layer 14. Also shown is the looped or woven layer 28 for portion 22 to attach to when wrapped around. Alternately, layer 28 could be eliminated, and portion 22 could be an adhesive for attaching to the back of cover layer 12.

Figure 4:
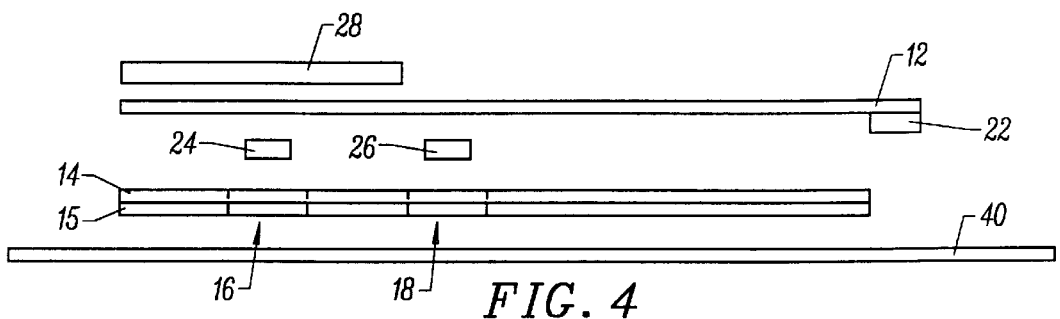
FIG. 4 is a side, disassembled view of the embodiment of FIG. 3.

FIG. 4 is a exploded view of the embodiment of FIG. 3 illustrating the components described above. Cover layer 12 could be a polyester or polyimide strip with metal traces deposited on it for providing the electrical connections, such as, for example, described in U.S. Pat. No. 5,469,845, the disclosure of which is hereby incorporated by reference.

The gel material used is preferably an oil plasticized thermoplastic elastomer gel, such as the triblock copolymer gels obtainable from Silipos of Niagara Falls, N.Y., and described in U.S. Pat. No. 4,369,284, Nos. 4,618,213, and No. 5,262,468, the disclosures of which are hereby incorporated by reference. Such gels are preferably mineral oil-based. When manufactured, such gels can be exposed to radiation sufficient to cause cross-linking. As described in more detail below for some of the following characteristics, such gels are pressure absorbing (i.e., they distribute pressure applied to a patient in order to limit pressure irritation or trauma to the skin), conform to the skin of the patient, have a mildly adhesive bond (i.e., they adhere to skin, yet can be peeled from sensitive skin without causing trauma), and spread heat generated by the emitter.

Support layer 14 can be a cloth-like, woven, or non-woven fibrous material. This support layer is used for attachment to gel layer 15, with the gel preferably being at least partially embedded in support layer 14. Protective layer 40 is a release liner applied over gel layer 15, which protects the gel layer and can be removed just before application to a patient.

Gel support layer 14 can be attached to cover layer 12 by any number of methods. For example, adhesives can be used. Alternately, to avoid delamination, ultrasonic welding can be used instead of an adhesive.

Figure 5:
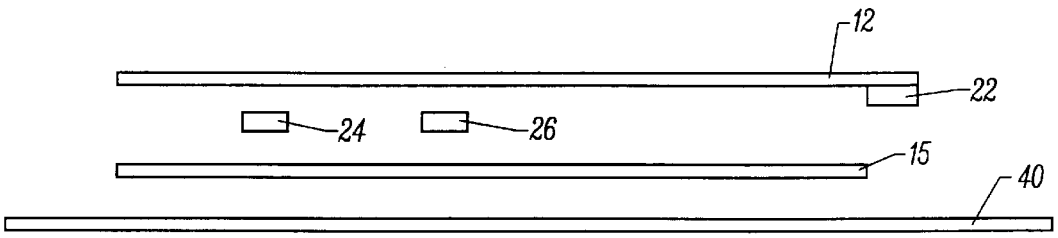
FIG. 5 is an alternate embodiment to that of FIG. 4 without a gel support layer.

FIG. 5 is a diagram of an alternate embodiment in which gel support layer 14 is eliminated. Instead, gel layer 15 is applied directly to cover layer 12. Another, separable feature of this embodiment is that holes 16 and 18 over the emitter and detector are eliminated.

Figure 6:
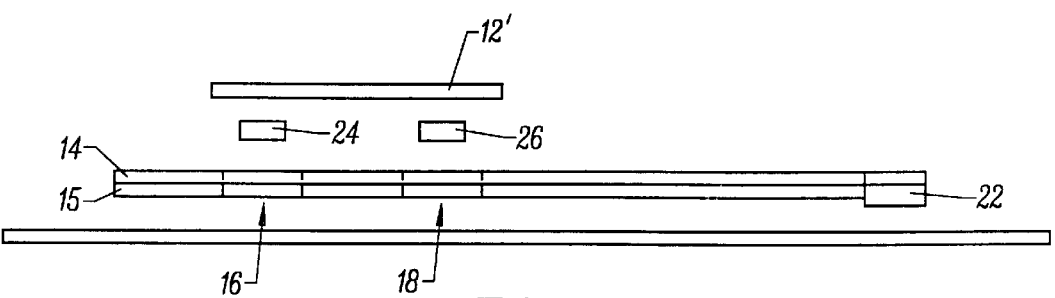
FIG. 6 is a side, disassembled view of an alternate embodiment of a sensor with a short cover layer.

FIG. 6 is yet another alternate embodiment in which cover layer 12' is shorter than cover layer 12 of FIGS. 3–5. The gel and support layers extend farther to allow them to wrap around an appendage. In an alternate embodiment, attachment layer 22 could be eliminated, with the gel layer attaching to its own backside, or to a cover layer such as 12 or 12', to secure the sensor to the patient. This embodiment reduces the thickness of the sensor, making it more flexible and less bulky.

The present invention also includes features designed to minimize undesirable light shunting from the emitter to the detector through the gel layer. Returning to FIG. 2, gap 52 in the gel and gel support layers exposes the underlying cover layer 12. Alternately, gap 52 could be filled with opaque material to reduce shunting.

The holes 16 and 18 above the emitter and detector prevent light being emitted or detected from scattering through the gel and inhibiting the effectiveness of the sensor. These holes also increase the efficiency of direct optical communication between emitter or detector and the human patient's tissue. If light enters the gel layer, the gel layer can act as a light pipe, directing light from emitter to detector without passing through the patient's tissue. This is one form of the phenomenon sometimes called optical shunt. The presence of holes 16 and 18 tend to reduce this effect. The break 52 in the gel layer is provided for the same purpose, to limit this shunting of light from the emitter to the detector. Alternately, a material that absorbs light may be placed adjacent to the gel in order to minimize shunting. For a further discussion of optical shunting and methods for minimizing it, reference is made to a copending application of the same assignee, entitled "Shunt Barrier in Pulse Oximeter Sensors," application Ser. No. 08/611,151, filed Mar. 5, 1996, the disclosure of which is incorporated herein by reference.

In alternate embodiments, the gel layer may be impregnated with a material which will scatter light and reduce light shunting. Preferably, the gel incorporates material which makes it opaque to at least some of the wavelengths emitted by emitter 24. In one embodiment, for a pulse oximeter sensor, the emitter consists of two light sources such as LEDs, one emitting light in the red region, and another emitting light in the infrared region. Preferably, the gel layer is substantially opaque to at least one of the wavelengths, more preferably it is substantially opaque to both of the wavelengths. In one embodiment, the gel has titanium dioxide impregnated into it, which gives it a white appearance and scatters the light from the emitter to reduce shunting. Alternately, a black pigment may be used. Any dye or pigment substantially opaque at the two wavelengths of the emitter may be used. Alternately, a substance that is substantially opaque at just one wavelength may be sufficiently useful.

To meet the requirement of substantial opacity, the materials of the sensor must somehow impede light that travels from emitter to detector, without going through the patient, to such an extent that the light which reaches the detector in this way has an acceptably small effect on the physiological measurement made by the sensor. This does not necessarily require the materials to be totally opaque, which is why the configuration of FIG. 5, in which light that interacts with the patient must pass through the gel layer, can work. As one quantitative example for typical sensors used in pulse oximetry, it would usually suffice for shunt light reaching the detector to be reduced sufficiently to induce a photocurrent of less than 1 nanoamp (nA) when the emitting LED is driven at 50 milliamps (mA). It would be still more desirable for shunt-induced photocurrent to be less than 0.1 nA. Because certain sensors are designed to work on patient sites where optical transmission through the patient's tissue is relatively high, it may be sufficient for a sensor designed for such a site to have photocurrent induced by optical shunt held to less than 10 nA. An example of such a site is the great toe of an infant for which the Nellcor Puritan Bennett I-20 Oxisensor II™ oximetry sensor is often used.

In an alternate embodiment, the gel can be opaque at wavelengths other than those used for physiological measurement, such as less than 600 nm, to protect against ambient light interference, as opposed to shunting. For example, the gel may be impregnated with material opaque at wavelengths of less than the wavelengths used in the emitters to avoid ambient light interference. Since the gel will often be thicker than a typical adhesive layer, there may be more opportunity for ambient light to enter around the sides when it is attached to a patient. In one embodiment, shunting may also be sufficiently avoided by having a break in the gel layer or holes in the gel layer. Thus, the material in the gel reduces ambient light interference, while the break in the gel reduces light shunting.

In one embodiment, the gel may be made conductive to shield the electronic components from electromagnetic interference (EMI), perhaps by incorporating silver chloride or indium tin oxide into the gel, for example.

The gel can also be used advantageously to spread heat generated by the emitter. In a thin, adhesive sensor, the emitter may be directly against the patient's skin, which may be problematic for very sensitive skin. By using a gel of sufficient thickness, the heat can be spread out before reaching the patient's skin so that the peak temperature induced by a given heat input is reduced. The heat spreading is caused by a combination of the thickness of the gel, the thermal conductivity of the gel, and in some designs by the presence of holes over the optics. Preferably, the gel is at least 0.005 inches thick.

The effectiveness of the skin-contacting layer of the sensor in spreading heat will rise as its thermal conductivity increases. An estimate of the desirable value of thermal conductivity may be made by considering the thermal conductivity of the skin itself. Literature reviews show that reported measurements of the thermal conductivity of human skin vary widely.

Cohen (Cohen, Myron L. (1977): Measurement of the thermal properties of human skin. A review. J. Invest. Dermatol. 69(3), 333–338.) cites values of 7.0 and $7.7 \times 10^{-4}$ cal/(cm·sec·C) for in vivo skin with different levels of perfusion. Cohen points out the importance of water content and perfusion intensity in determining the effective conductivity. Since the same lower limit appears in Cohen's survey for excised and in vivo skin, we see $7 \times 10^{-4}$ cal/(cm·sec·C) as the lowest value he would propose for dry non-perfused skin. Multiplying by 418.4 to convert units, we obtain a range of 0.29 to 2.80 W/(m·K).

Another literature review, (Bowman, HF; Cravalho, EG; Woods, M (1975): Theory, measurement and application of thermal properties of biomaterials. Ann. Rev. 4, 43–80.), cites a list of references which partially overlap Cohen's list, to give a range of 0.23 to 2.87 W/(m·K). We may therefore take 0.23 W/(m·K) as the minimum value that is at all likely to be observed in skin.

It is therefore desirable for the thermal conductivity of the skin-contacting layer of the sensor to be at least half that of skin, or 0.12 W/(m·K). Preferably the thermal conductivity of the skin-contacting layer should be at least 0.23 W/(m·K), and most preferably it should exceed that of water, which is 0.6 W/(m·K).

Figure 7:
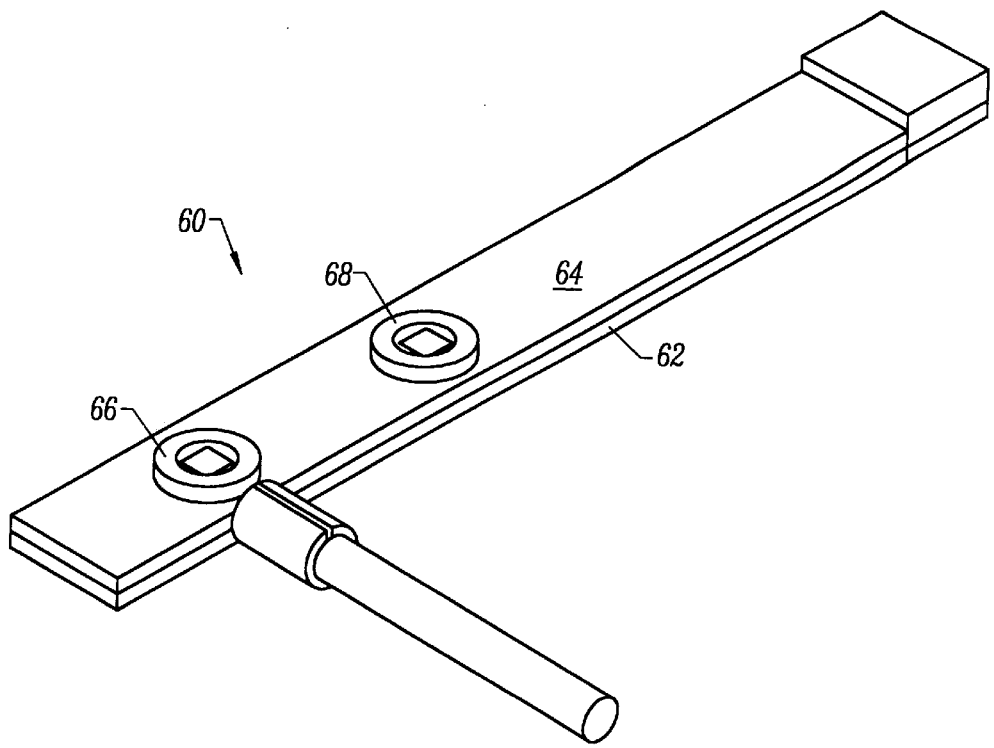
FIG. 7 is a perspective view of an alternate embodiment showing doughnut-shaped gel pads on a sensor.

FIG. 7 is an alternate embodiment of the present invention showing a sensor 60 having a cover layer 62 and a non-gel top layer 64 covering the electronics, with openings over the emitter and detector. Doughnut-shaped gel pads 66 and 68 are used to provide the limited adhesiveness needed around the emitter and detector areas of attachment to the patient. Alternately, a series of gel dots or other shapes could be used. Preferably, the gel doughnuts or dots are located around the optics of the sensor. Thus, the patient's skin is contacted only by totally non-adhesive materials such as 64, or by mildly adhesive materials such as 66 and 68, where such materials may be needed in the immediate vicinity of sensor optics to reduce motion sensitivity in the sensor. Another possibility would involve no holes in the gel dots which could further reduce motion sensitivity while minimizing adhesive area. An example of a conformable sensor using an adhesive to reduce motion artifact is set forth in U.S. Pat. No. 5,246,003, issued Sep. 21, 1993, and incorporated herein by reference.

Figure 8:
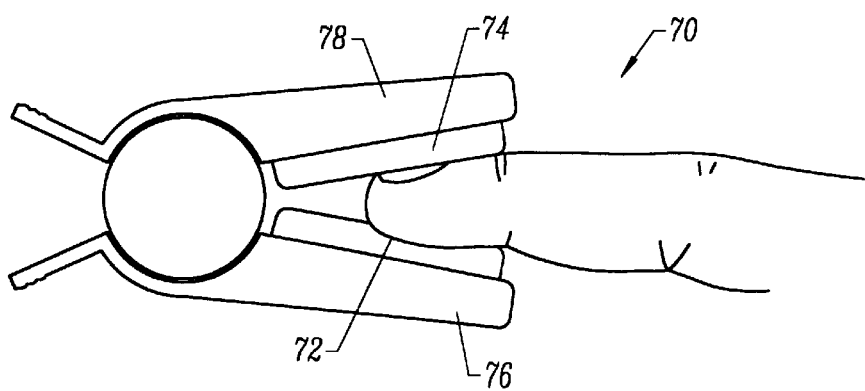
FIG. 8 is a side view of an alternate embodiment showing gel pads in a clip-type sensor.

FIG. 8 shows yet another embodiment of the invention in which a clip-type sensor 70 includes a pair of gel pads 72 and 74 mounted inside of clip arms 76 and 78, respectively. The gel pads 72 and 74 can have the gel exposed, or can have the gel enclosed within a flexible shell material, such as a plastic.

Alternate embodiments are also possible. For example, instead of the long strip of FIGS. 1–7, a sensor with wings could be used, with the wings folded around to contact the back side (i.e., see U.S. Pat. No. 4,830,104, incorporated herein by reference). In one embodiment, rather than using Velcro™, the gel itself could be used to contact the back side of the sensor cover layer 12 and provide sufficient adhesion to hold the sensor in place. Alternately, or in addition, the sensor could be wrapped with a bandage to hold it in place, such as a stretchable, elastic and cloth wrap.

In one embodiment, where the gel is embedded with a conductive material for EMI shielding, the gel is in contact with a copper or other shield. Such a shield may be the shielding around cable 20 of FIG. 1, with the shielding connecting through the top of support layer 14 to the gel layer 15.

Although the gel manufactured by Silipos is described above, alternate gels may be used. For example, the gel support layer may be used with any gel, such as hydrogels. The gel support layer could provide sufficient support to make the hydrogel easy to handle. In one embodiment, the gel is embedded in the gel support layer before curing, to provide better contact. Although a woven, non-woven, or cloth-based support layer is described, any material which is at least semipermeable or porous to the gel can be used.

The gel sensor, when manufactured, is preferably stored in a vapor permeable pouch to allow sterilization. This allows the sensor to be sterilized in the pouch with ethylene oxide, while allowing the ethylene oxide to escape after the sterilization step without requiring removal from the pouch. A gel which will not dry out for a reasonable period of time in a vapor permeable pouch is preferred, and the above described Silipos gels meet this requirement. Hydrogel, for example, may need a vapor impermeable pouch to avoid drying out over a period of time. The ability to easily sterilize allows the gel sensor of the present invention to either be a single use sensor or a reusable sensor.

Preferably, in order to minimize damaging a patient's sensitive skin, the gel has an adhesion force of less than that of current adhesive oximetry sensors, such as the Nellcor Puritan Bennett N-25. The adhesion force is preferably no more than a value of 50 ounce/inch (according to ASTM D3330). More preferably, a value of less than 20 ounce/inch is used. In addition, a gel which is insoluble in water is preferably used to avoid contamination of the gel due to spills, urine, etc. Additionally, the gel is preferably resistant to drying, so that it will not dry out for at least five days when exposed to ambient air. This will improve both the shelf life and the duration of time the gel can be effective when applied to a patient. When using the mineral oil gel, it has an additional benefit of conditioning the skin.

A mechanically compressed gel has the additional benefit of sealing out water. The gel used preferably has sufficient adhesiveness to stick to the skin without having such high adhesion force that the skin would tear upon removal. The gel will additionally dissipate the heat generated by the emitters over a large area, if the gel covers the entire portion of the front surface of the sensor which contacts the subject's tissue.

The term "gel" as used herein refers to a material which has a cohesive force greater than its adhesive force and produces a uniform, adhesive bond. Gels can be manufactured, for example, by casting, extrusion, dipping and coating. In addition, a gel is generally soft and conformable to the touch.

The gel material should accommodate and distribute bandage pressure, the pressure preferably accommodated by the material's inherently shock absorbing nature. The material should be soft and flexible in order to easily conform to the skin. The material should removably adhere to the skin in a non-irritating and non-drying manner, having bonding characteristics with the skin that permit the material to be easily removed without causing trauma to the skin nor damage to the material. The material should be elastomeric, having sufficient integrity to repeatedly permit such easy removal. The material should preferably have sufficiently stable and long-lived properties that would make it reusable and resistant to contamination.

A gel can be moldably manufactured using a shape-preserving, elastomeric (stretchable and inherently pressure compressible), polymeric matrix. It is this matrix which inherently acts to absorb bandage stress. The gel can be made sufficiently soft and flexible based upon controlling the degree of polymer cross-linking using plasticers. This matrix is impregnated with a suitably inert, non-drying matrix filling fluid and thermoplastically molded in order to provide an integral and stable material having the desired adhesive bond adherence (physical and mechanical properties) to sensitive skin which enables the gel to easily and repeatedly "peel" away from the skin without causing trauma to the skin.

As will be understood by those with skill in the art, the present invention may be embodied in other specific forms without departing from the spirit or essential characteristics thereof. For example, the emitter could emit other types of radiation than light. Accordingly, the foregoing description is illustrative of the invention, but not limiting of the scope of the invention, which is set forth in the following claims.

What is claimed is:

1. A sensor comprising:
   a cover layer;
   an emitter disposed on a first side of said cover layer;
   a detector disposed on said first side of said cover layer; and
   an oil plasticized thermoplastic elastomer gel disposed on said first side of said cover layer, said gel being an outside layer for direct contact with a patient.

2. The sensor of claim 1 wherein said gel contains mineral oil.

3. The sensor of claim 1 further comprising holes in said gel over at least one of said emitter and detector.

4. The sensor of claim 1 further comprising a break in said gel between said emitter and said detector, said break having sufficient width to reduce radiation shunting from said emitter to said detector through said gel.

5. The sensor of claim 1 further comprising an at least partially opaque material incorporated in said gel between said emitter and said detector.

6. The sensor of claim 1 further comprising:
   a plurality of flexible hooks mounted on said first side of said cover layer adjacent an end of said cover layer; and
   a plurality of loops for attachment to said hooks on a second side of said cover layer.

7. The sensor of claim 1 further comprising an adhesive disposed on said first side of said cover layer adjacent an end of said cover layer for attaching to a second side of said cover layer.

8. The sensor of claim 1 wherein said gel has a thickness of greater than 0.005 inches.

9. The sensor of claim 1 wherein said sensor is a pulse oximeter sensor.

10. The sensor of claim 1 further comprising a vapor permeable, water impermeable, pouch enclosing said sensor.

11. The sensor of claim 1 wherein said gel has a thermal conductivity greater than 0.20 W/(m*K).

12. The sensor of claim 1 further comprising:
    a gel support layer disposed on said first side of said cover layer; and
    said gel being embedded in said gel support layer.

13. The sensor of claim 12 wherein said gel support layer is a woven material.

14. The sensor of claim 12 wherein said gel support layer is a fibrous material.

15. The sensor of claim 1 wherein said gel is substantially opaque to selected wavelengths of radiation.

16. The sensor of claim 15 wherein said selected wavelengths include at least some of the wavelengths of radiation emitted by said emitter.

17. A method of manufacturing a sensor, comprising the steps of:
    providing a cover layer;
    disposing an emitter on a first side of said cover layer;
    disposing a detector on said first side of said cover layer; and
    disposing an oil plasticized thermoplastic elastomer gel on said first side of said cover layer, said gel being an outside layer which can be exposed and placed in direct contact with a patient.

18. The method of claim 17 further comprising the steps of:
    embedding said gel in a support layer; and
    disposing said support layer onto said first side of said cover layer.

19. The method of claim 18 further comprising the step of bonding said support layer and gel to said cover layer using ultrasonic welding.

20. The method of claim 17 further comprising the steps of:
    using mineral oil in said gel; and
    subjecting said gel to radiation sufficient to cause cross-linking.

21. The method of claim 17 further comprising the step of incorporating radiation scattering particles in said gel.

22. A sensor comprising:
    a cover layer;
    an emitter disposed on a first side of said cover layer;
    a detector disposed on said first side of said cover layer; and
    a mineral oil based gel disposed on said first side of said cover layer, said gel being an outside layer for direct contact with a patient.

23. The sensor of claim 22 further comprising holes in said gel over at least one of said emitter and detector.

24. The sensor of claim 22 further comprising a break in said gel between said emitter and said detector, said break having sufficient width to reduce radiation shunting from said emitter to said detector through said gel.

25. The sensor of claim 22 further comprising:
a gel support layer disposed on said first side of said cover layer; and
said gel being embedded in said gel support layer.

26. The sensor of claim 22 further comprising:
means for reducing shunt radiation to said detector to a level which results in less than 10 nA of shunt current produced by said detector.

27. An pulse oximeter sensor comprising:
a cover layer;
an emitter disposed on a first side of said cover layer;
a detector disposed on said first side of said cover layer;
a support layer mounted on said first side of said cover layer; and
a gel embedded in said support layer, said gel and support layer forming an outside layer for direct contact with a patient.

28. The sensor of claim 27 wherein said support layer is a woven material.

29. The sensor of claim 27 wherein said support layer is a fibrous material.

30. The sensor of claim 27 further comprising:
a plurality of flexible hooks mounted on said first side of said cover layer adjacent an end of said cover layer; and
a plurality of loops for attachment to said hooks on a second side of said cover layer.

31. The sensor of claim 27 further comprising an adhesive disposed on said first side of said cover layer adjacent an end of said cover layer for attaching to a second side of said cover layer.

32. The sensor of claim 27 wherein said gel has a thickness of greater than 0.005 inches.

33. The sensor of claim 27 further comprising:
means for reducing shunt radiation to said detector to a level which results in less than 10 nA of shunt current produced by said detector.

34. A sensor comprising:
a cover layer;
an emitter disposed on a first side of said cover layer;
a detector disposed on said first side of said cover layer;
a gel mounted on said first side of said cover layer, said gel being an outside layer for direct contact with a patient; and
means for reducing shunt radiation to said detector to a level which results in less than 10 nA of shunt current produced by said detector.

35. The sensor of claim 34 wherein said means for reducing shunt radiation comprises said gel being substantially opaque to selected wavelengths of radiation.

36. The sensor of claim 34 wherein said shunt current is less than one nA.

37. The sensor of claim 34 wherein said shunt current is less than 0.1 nA.

38. The sensor of claim 34 wherein said means for reducing shunt radiation comprises an at least partially opaque material incorporated into said gel between said emitter and said detector.

39. The sensor of claim 34 wherein said means for reducing shunt radiation comprises an optically scattering material incorporated into said gel between said emitter and said detector.

40. The sensor of claim 34 wherein said means for reducing shunt radiation comprises an optically absorptive material incorporated into said gel between said emitter and said detector.

41. The sensor of claim 34 wherein said means for reducing shunt radiation comprises a break in said gel between said emitter and said detector.

42. A sensor comprising:
a cover layer;
an emitter disposed on a first side of said cover layer;
a detector disposed on said first side of said cover layer; and
a gel disposed on said first side of said cover layer, said gel being electrically conductive, said gel being an outside layer for direct contact with a patient.

43. The sensor of claim 42 further comprising an electrical shield connected to said gel.

44. A sensor comprising:
a cover layer;
an emitter disposed on a first side of said cover layer;
a detector disposed on said first side of said cover layer;
a gel disposed on said first side of said cover layer, said gel being an outside layer for direct contact with a patient; and
wherein said gel defines holes over said emitter and detector such that radiation transmissions to and from said detector and emitter need not pass through said gel.

45. The sensor of claim 44 further comprising:
a gel support layer disposed on said first side of said cover layer; and
said gel being embedded in said gel support layer.

46. The sensor of claim 44 wherein said gel contains mineral oil.

47. The sensor of claim 44 wherein said gel has a thickness of greater than 0.005 inches.

48. The sensor of claim 44 wherein said sensor is a pulse oximeter sensor.

49. The sensor of claim 44 further comprising:
means for reducing shunt radiation to said detector to a level which results in less than 10 nA of shunt current produced by said detector.

50. A sensor comprising:
a cover layer;
an emitter disposed on a first side of said cover layer;
a detector disposed on said first side of said cover layer;
a gel disposed on said first side of said cover layer, said gel being an outside layer for direct contact with a patient; and
wherein said gel defines a break between said emitter and detector to reduce radiation shunting from said emitter to said detector.

51. The sensor of claim 50 further comprising a substantially opaque material mounted in said break.

52. The sensor of claim 50 further comprising:
a gel support layer disposed on said first side of said cover layer; and
said gel being embedded in said gel support layer.

53. The sensor of claim 50 wherein said gel contains mineral oil.

54. The sensor of claim 50 wherein said gel has a thickness of greater than 0.005 inches.

55. The sensor of claim 50 wherein said sensor is a pulse oximeter sensor.

56. The sensor of any one of claims 1, 22, 27, 34, 42, 44 and 50 further comprising an impedance for indicating a characteristic of said emitter.

57. The sensor of any one of claims 1, 22, 27, 34, 42, 44 and 50 further comprising an additional sensing element.

58. The sensor of claim 57 wherein said additional sensing element is an EKG sensor.

* * * * *